US006459931B1

(12) United States Patent
Hirschman

(10) Patent No.: US 6,459,931 B1
(45) Date of Patent: Oct. 1, 2002

(54) APPARATUSES AND METHODS FOR EXTRAVASATION DETECTION

(75) Inventor: Alan D. Hirschman, Glenshaw, PA (US)

(73) Assignee: Medrad, Inc., Indianola, PA (US)

( * ) Notice: Subject to any disclaimer, the term of this patent is extended or adjusted under 35 U.S.C. 154(b) by 0 days.

(21) Appl. No.: 10/006,087

(22) Filed: Dec. 5, 2001

Related U.S. Application Data

(62) Division of application No. 09/362,384, filed on Jul. 28, 1999, now Pat. No. 6,408,204.

(51) Int. Cl.[7] .................................................. A61B 5/00

(52) U.S. Cl. ..................... 600/547; 600/382; 600/384; 600/393

(58) Field of Search ................................. 600/382, 384, 600/393, 547; 604/116

(56) References Cited

U.S. PATENT DOCUMENTS

| | | |
|---|---|---|
| 3,779,079 A | 12/1973 | Snook |
| 4,010,749 A | 3/1977 | Shaw |
| 4,378,808 A | 4/1983 | Lichtenstein |
| 4,572,182 A | 2/1986 | Royse |
| 4,647,281 A | 3/1987 | Carr |
| 4,648,869 A | 3/1987 | Bobo, Jr. |
| 4,653,501 A | 3/1987 | Cartmell et al. |
| 4,667,679 A | 5/1987 | Sahota |
| 4,816,019 A | 3/1989 | Kamen |
| 4,877,034 A | 10/1989 | Atkins et al. |
| 4,959,050 A | 9/1990 | Bobo, Jr. |
| 5,026,348 A | 6/1991 | Venegas |
| 5,334,141 A | 8/1994 | Carr et al. |
| 5,947,910 A | 9/1999 | Zimmet |
| 5,954,668 A | 9/1999 | Uber, III et al. |
| 5,964,703 A | 10/1999 | Goodman et al. |

FOREIGN PATENT DOCUMENTS

| | | |
|---|---|---|
| JP | 11-57001 | 3/1999 |
| WO | WO 99/26685 | 6/1999 |
| WO | WO 99/26686 | 6/1999 |
| WO | WO 99/29356 | 6/1999 |
| WO | WO 01/08729 | 2/2001 |

OTHER PUBLICATIONS

Carr, K. L., "Use of Gallium Arsenide in Medical Applications," IEEE Gallium Arsenide Integrated Circuits (GAAS IC) Symposium, US, New York, IEEE, vol. SYMP. 17, Oct. 29, 1995, pp. 10–13.

Shaeffer, Ph.D., "Detection of Extravasation of Antineoplastic Drugs by Microwave Radiometry," Cancer Letters, 31 (1986), p. 285–291.

Shaeffer, Ph.D., "Early Detection of Extravasation of Radiographic Contrast Medium," 141–144, Contrast Media Radiology, Jul. 1992).

"MMIC Receiver for Water–Vapor Radiometer," NASA Tech. Briefs, Sep. 1993; 34.

(List continued on next page.)

Primary Examiner—Max Hindenburg
(74) Attorney, Agent, or Firm—Henry E. Bartony, Jr.; Gregory L. Bradley

(57) ABSTRACT

An apparatus for the detection of extravasation is positioned in a manner so that the vicinity of a site is available for palpation and is visible for visual inspection. Another embodiment of the apparatus improves the sensitivity of detection by positioning an energy source and a receiver between a first layer of a high dielectric material and a second lay of a low dielectric material. The apparatus may further include a third layer of a conductive material to shield the apparatus from stray capacitance. In addition, a system for detection of extravasation includes an array of sensors located at, adjacent to and/or remote from an injection site.

20 Claims, 7 Drawing Sheets

OTHER PUBLICATIONS

Arkin, "Recent Developments in Modeling Heat Transfer in Blood Perfused Tissues," IEEE Transactions on Biomedical Engineering, vol. 41, No. 2, Feb. 1994; 97–107.

Harris & Von Maltzahn, "Infusion Line Model for the Detection of Infiltration Extravasation and Other Fluid Flow Faults," IEEE Transactions on Biomedical Engineering, vol. 40, No. 2, Feb. 1993, 154–162.

Montreuil & Nachman, "Multiangle Method for Temperature Measurement of Biological Tissues by Microwave Radiometry," IEEE Transactions on Microwave Theory and Techniques, vol. 39, No. 7, Jul. 1991, 1235–1238.

International Search Report for Counterpart PCT Application PCT/US 00/20112.

APPARATUSES AND METHODS FOR EXTRAVASATION DETECTION

CROSS-REFERENCE TO RELATED APPLICATION

This application is a division of application Ser. No. 09/362,384, filed on Jul. 28, 1999 now U.S. Pat. No. 6,408,204, the contents of which are hereby incorporated by reference.

BACKGROUND OF THE INVENTION

The present invention relates generally to the detection of extravasation of fluids injected into the vascular system, and, more particularly, to extravasation detection devices and methods in medical injection procedures using electrical energy transmission through tissue in the vicinity of an injection site or other site.

In many medical diagnostic and therapeutic procedures, a physician or other person injects a patient with a fluid. In recent years, a number of injector-actuated syringes and powered injectors for pressurized injection of contrast medium in procedures such as angiography, computed tomography, ultrasound and NMR/MRI have been developed.

Extravasation is the accidental infusion of an injection fluid such as a contrast medium into tissue surrounding a blood vessel rather than into the blood vessel itself. Extravasation can be caused, for example, by fragile vasculature, valve disease, inappropriate needle placement, or patient movement resulting in the infusing needle being pulled from the intended vessel or causing the needle to be pushed through the wall of the vessel. Furthermore, high injection pressures and/or rates of some modern procedures increase the risk of extravasation. In computed tomography, for example, contrast injection flow rates can be in the range of 0.1 to 10 ml/s.

Moreover, extravasation can cause serious injury to patients. In that regard, certain injection fluids such as contrast media or chemotherapy drugs can be toxic to tissue if not diluted by blood flow. It is, therefore, very important when performing fluid injections to detect extravasation as soon as possible and discontinue the injection upon detection.

Several extravasation techniques are known in the art. Two simple and very useful techniques for detecting extravasation are palpation of the patient in the vicinity of the injection site and simple visual observation of the vicinity of the injection site by a trained health care provider. In the palpation technique, the health care provider manually senses swelling of tissue near the injection resulting from extravasation. By visual observation, it is also sometimes possible to observe directly any swelling of the skin in the vicinity of an injection site resulting from extravasation.

In addition to palpation and observation, there are a number of automatic methods of detecting extravasation that include automatically triggering an alarm condition upon detection. For example, U.S. Pat. No. 4,647,281 discloses subcutaneous temperature sensing of extravasation to trigger such an alarm. In this method of extravasation detection, an antenna and a microwave radiometer instantaneously measure the temperature of the subcutaneous tissue at the site where fluid is injected. An algorithm periodically determines the temperature difference between tissue and injected fluid, and compares the difference to a fixed threshold. An alarm processor uses the comparison to determine an alarm condition.

In addition, U.S. Pat. No. 5,334,141 discloses a microwave extravasation detection system employing a reusable microwave antenna and a disposable attachment element for releasably securing the microwave antenna to a patient's skin over an injection site. The attachment element holds the antenna in intimate contact with the patient's skin to optimize microwave transfer therebetween, while shielding the antenna from environmental noise signals.

Several plethysmographic detection techniques are available in addition to known temperature sensing techniques. For example, mercury strain gauge plethysmographs measure the volume change resulting from venous blood flow in a cross sectional area of a limb of a patient. Air cuff or pulse volume recorder plethysmographs measure the changes in pressure within a recording cuff caused by the change in volume of a limb or digit as a result of extravasation. Photo-plethysmographs measure the optical scattering properties of capillary blood to detect the presence of extravasated fluids in tissue. An example of a photo-plethysmograph is described in U.S. Pat. No. 4,877,034.

Impedance plethysmographs measure changes in the electrical impedance in a defined tissue volume of a limb. In this method, an impedance change of a certain level in the vicinity of the injection site is interpreted as being an extravasation. A change in impedance occurs during extravasation because injection fluid in the tissue of the patient changes both the volume and the electrical impedance properties of the tissue. An example of an impedance measurement device for sensing extravasation of radiographic contract medium is the EDA™ patch manufactured by E-Z-EM, Co. of Westbury, N.Y. Maintaining suitable electrical contact between the electrodes of similar impedance plethysmographs and the skin of the patient, however, is often very difficult in such impedance measuring devices.

Although the EDA patch is capable of providing extravasation detection at speeds required by high injection-rate procedures when good electrical contact is maintained, the placement of the patch over the injection site prevents simultaneous performance of unobstructed palpation and visual examination by the health care provider. Other automatic methods for detecting extravasation also result in obstruction of the injection site and prevent palpation and visual observation. In the case of the photo-plethysmograph, for example, it is also critical to make direct contact with the skin to sense small changes in light scattering from the superficial layers of tissue. Unfortunately, preventing palpation and visual observation eliminates a valuable warning of the occurrence of extravasation.

It is, therefore, very desirable to develop improved devices and methods for detecting extravasation during the high flow rate procedures (1 to 10 ml/sec) typically encountered in angiographic, CT, ultrasound, and MR imaging procedures.

SUMMARY OF THE INVENTION

The present invention provides generally a device and method for the detection of extravasation in an injection procedure including at least a first energy source for supplying energy to tissue in the vicinity of a site and at least a first receiver to measure a signal resulting from changes in the energy supplied to the tissue by the first energy source. The signal will change when extravasation occurs due to a change in the bulk electrical properties of tissue and injected fluid in the region of the extravasation. Unlike prior devices for the detection of extravasation, the first energy source and the first receiver are positioned in a manner so that the vicinity of an injection site or other site is available for manual palpation and is visible for visual inspection.

In several embodiments, the energy source and the receiver contact the skin of a patient. In one embodiment, the device includes a base (for example, a patch) incorporating a sensor or transducer including the first energy source and the first receiver. Such a base or patch preferably has an open portion so that the vicinity of a site is available for palpation and is visible for visual inspection. Alternatively, the first energy source may be incorporated in a first base or patch and the first receiver may be incorporated in a second base or patch so that the vicinity of the site is unobstructed.

The device of the present invention preferably includes at least a second energy source to supply energy to tissue in the vicinity of the site, and at least a second receiver to measure a second signal resulting from the energy supplied to the tissue by the second energy source. The multiple energy source/receiver pairs of the present invention can be incorporated in a single or multiple bases or patches as described above. The energy source/receiver pairs are preferably oriented differently with respect to the tissue in the vicinity of the site.

In another embodiment of the present invention, the first energy source and the first receiver do not contact the skin of a patient and, therefore, keep the vicinity of the site available for palpation and visible for visual inspection. For example, the first energy source may include a source of radio frequency energy and the first receiver may include a coil. In this embodiment, the device measures inductive impedance of a region of the tissue. The first receiver may also include two coils so that the device measures the inductive coupling of the two coils.

The present invention also provides a device for the detection of extravasation in an injection procedure including a first energy source to supply energy to tissue in the vicinity of an injection site or in the vicinity of another site remote from the injection site and a first receiver to measure a first signal resulting from the energy supplied to the tissue by the first energy source. The device further includes at least a second energy source to supply energy to tissue in the vicinity of the site and at least a second receiver to measure a second signal resulting from the energy supplied to the tissue by the second energy source. The first energy source and first receiver pairing are orientated differently with respect to the site from the second energy source and second receiver pairing. In this manner, measurements across different orientations of the tissue in the vicinity of the site can be maintained. Preferably, the first energy source and first receiver pairing is oriented generally orthogonal to the second energy source and second receiver pairing.

The present invention also provides a device for the detection of extravasation in an injection procedure including a first layer of a material with relatively high dielectric constant. Preferably, the first layer of material has a dielectric constant of at least approximately 5. An example of a suitable material for the first layer is vinylidene fluoride film (for example, Kynar™ available from Elf Atochem), having a dielectric constant of approximately 7. The device also includes a second layer of a relatively low dielectric material. Preferably, the material of the second layer has a dielectric constant of less than approximately 4. An example of a suitable material for the second layer is a polyimide film (for example, Kapton™, available from Dupont, Inc.), having a dielectric constant of approximately 3.5. The device further includes at least one energy source/receiver pairing as described above. The energy source and the receiver are positioned between the first layer and the second layer. The second layer is positioned outside of the first layer relative to the tissue. A layer of a hydrogel material may be positioned between the first layer and the tissue to improve electrical coupling.

The device may further include a third layer of a conductive material such as a thin film of indium-tin oxide. The third layer is positioned outside of the second layer relative to the tissue and is of sufficient conductivity to shield the device from stray capacitance which can drain electrical energy from the exposed combination of electrodes and tissue, thereby reducing the sensitivity of measurement.

The present invention still further provides a device for the detection of extravasation in an injection procedure including an energy source/receiver pairing as described above and a layer of a conductive material to shield the device from stray capacitance.

In some patients, extravasation sometimes occurs at a site remote from the catheter insertion point (that is, the injection site). The present invention thus also provides a method for detecting extravasation in an injection procedure comprising the step of positioning at least a first sensor adapted to detect extravasation at a position or site remote from an injection site, but along a path of potential extravasation. A second sensor adapted to detect extravasation is preferably also positioned in a vicinity of the injection site.

The present invention also provides a system for the detection of extravasation in an injection procedure including a first sensor positioned to detect extravasation in the vicinity of an injection site and at least a second sensor positioned to detect extravasation at a site remote from the injection site. An array of such sensors or transducers can be provided along a path of potential extravasation.

Such sensors can be formed as described above. For example, the first sensor may include at least a first energy source to supply energy to tissue in the vicinity of a site and at least a first receiver for measuring a signal resulting from the energy supplied to the tissue by the first energy source. The first energy source and the first receiver are preferably positioned in a manner so that the vicinity of the site is available for palpation and is visible for visual inspection.

The present invention also provides a method of detecting extravasation in an injection procedure including the steps of: positioning a first energy source and a first receiver in a manner so that the vicinity of a site is available for palpation and visible for visual inspection, applying energy to tissue in the vicinity of the site via the first energy source, and measuring a signal resulting from the energy supplied to the tissue by the first energy source with the first receiver.

The present invention further provides a method for detecting extravasation in an injection procedure comprising the steps of: positioning a first sensor in a first orientation relative to a site, positioning at least a second sensor in a second orientation, different from the first orientation, relative to the site. As described above, the first sensor may include a first energy source to supply energy to tissue in the vicinity of the site and a first receiver to measure a first signal resulting from the energy supplied to the tissue by the first energy source. Likewise, the second sensor may include a second energy source to supply energy to tissue in the vicinity of the site and a second receiver to measure a second signal resulting from the energy supplied Lo the tissue by the second energy source.

The present invention also provides a method for detecting extravasation in an injection procedure performed on a patient including the steps of: positioning an energy source and a receiver between a first layer of a high dielectric material and a second layer of a low dielectric material, the second layer being positioned outside of the first layer relative to the patient, supplying energy to tissue in the vicinity of an injection site via the energy source, and measuring a resulting signal with the receiver.

Still further, the present invention provides a method for detecting extravasation in an injection procedure comprising the steps of: supplying energy to tissue in the vicinity of an injection site via an energy source, measuring a resulting signal with a receiver, and shielding the energy source and the receiver from stray capacitance with a conductive material.

The present invention and its attendant advantages will be further understood by reference to the following detailed description and the accompanying drawings.

DETAILED DESCRIPTION OF THE INVENTION

Figure 1:
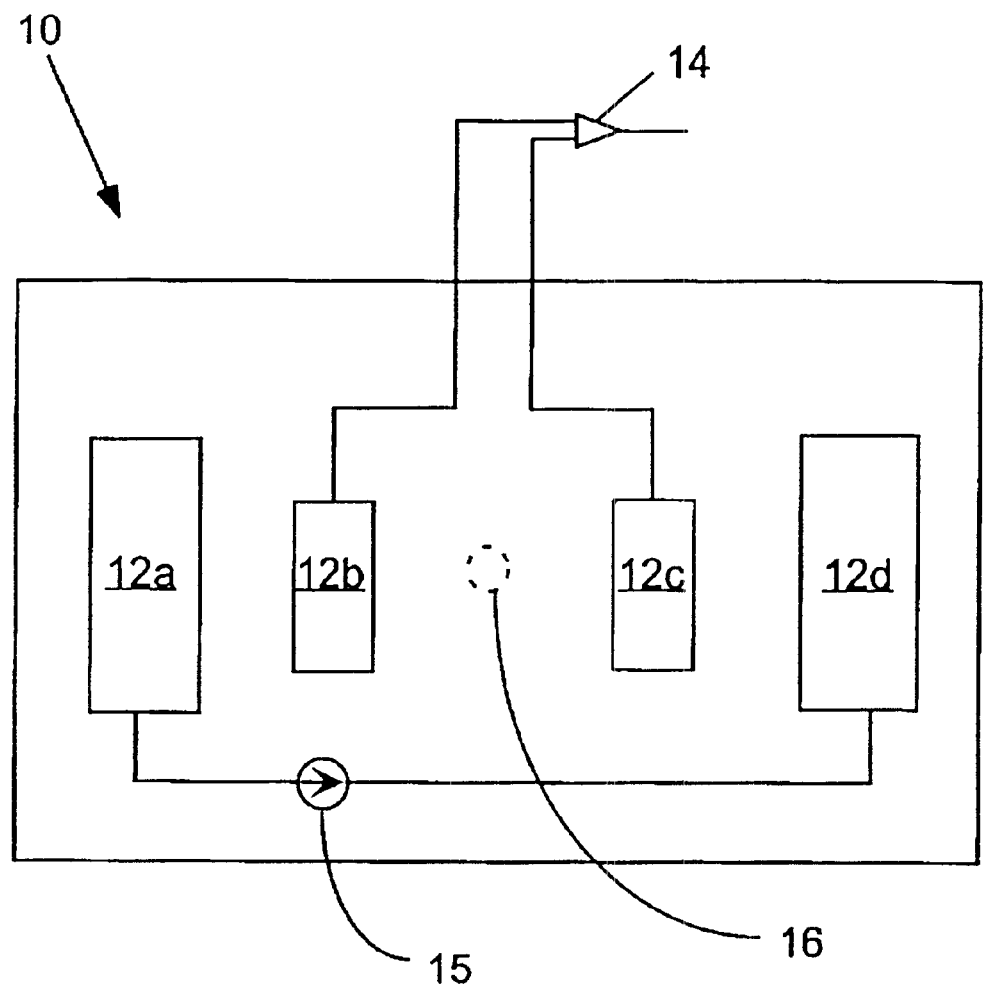
FIG. 1 illustrates a currently available tetrapolar impedance plethysmograph transducer.

Referring to FIG. 1, a prior art transducer for an electrical impedance plethysmograph 10, such as the EDA™ patch manufactured by E-Z-EM, Co. of Westbury, N.Y., is illustrated. Transducer 10 can be applied to an extremity of a patient to detect extravasation during injection of a fluid into the patient at an injection site. Transducer 10 is positioned so that the injection site is covered by the approximate geometric center of the device.

Transducer 10 includes four electrodes 12a–d. Electrodes 12a–d can be formed of a mixture of silver/silver chloride or any other suitable conductive material. When transducer 10 is applied to a patient to detect extravasation, electrodes 12a–d can be placed in direct ohmic contact with the skin or can be offset slightly from the skin through capacitive coupling with the skin of the patient in the vicinity of the injection site. In a conventional use of transducer 10, a constant current source 15 of radio frequency (RF) energy is applied to the region of injection site 16 by way of electrodes 12a–d. The applied RF energy can have a frequency, for example, in the range of one kilohertz to one megahertz.

Transducer 10 also includes a high impedance amplifier 14. High impedance amplifier 14 has two inputs. One of the inputs of amplifier 14 is coupled to electrode 12b, while the other input is coupled to electrode 12c. In this manner amplifier 14 is coupled to receive and amplify a voltage difference between electrodes 12b and 12c when energy is applied to the patient by way of electrodes 12a and 12d. If extravasation occurs in the vicinity of injection site 16, it causes both a volume change resulting from swelling in the region of transducer 10 and a conductivity change, thereby changing the electrical impedance sensed by electrodes 12b and 12c. A change in impedance in the region causes a change in the voltage detected by high impedance amplifier 14. In this manner, extravasation is detected and injection of the fluid into the patient can be terminated immediately or a warning signal can be generated for the operator.

It will be understood by those skilled in the art that it is sometimes difficult to obtain good ohmic contact between electrodes 12a–d and the skin of a patient. Poor ohmic contact can be caused by factors such as natural moisture on the skin of the patient where electrodes 12a–d are applied. Thus, it is sometimes preferred that a plethysmograph operate by means of capacitive coupling.

Figure 2:
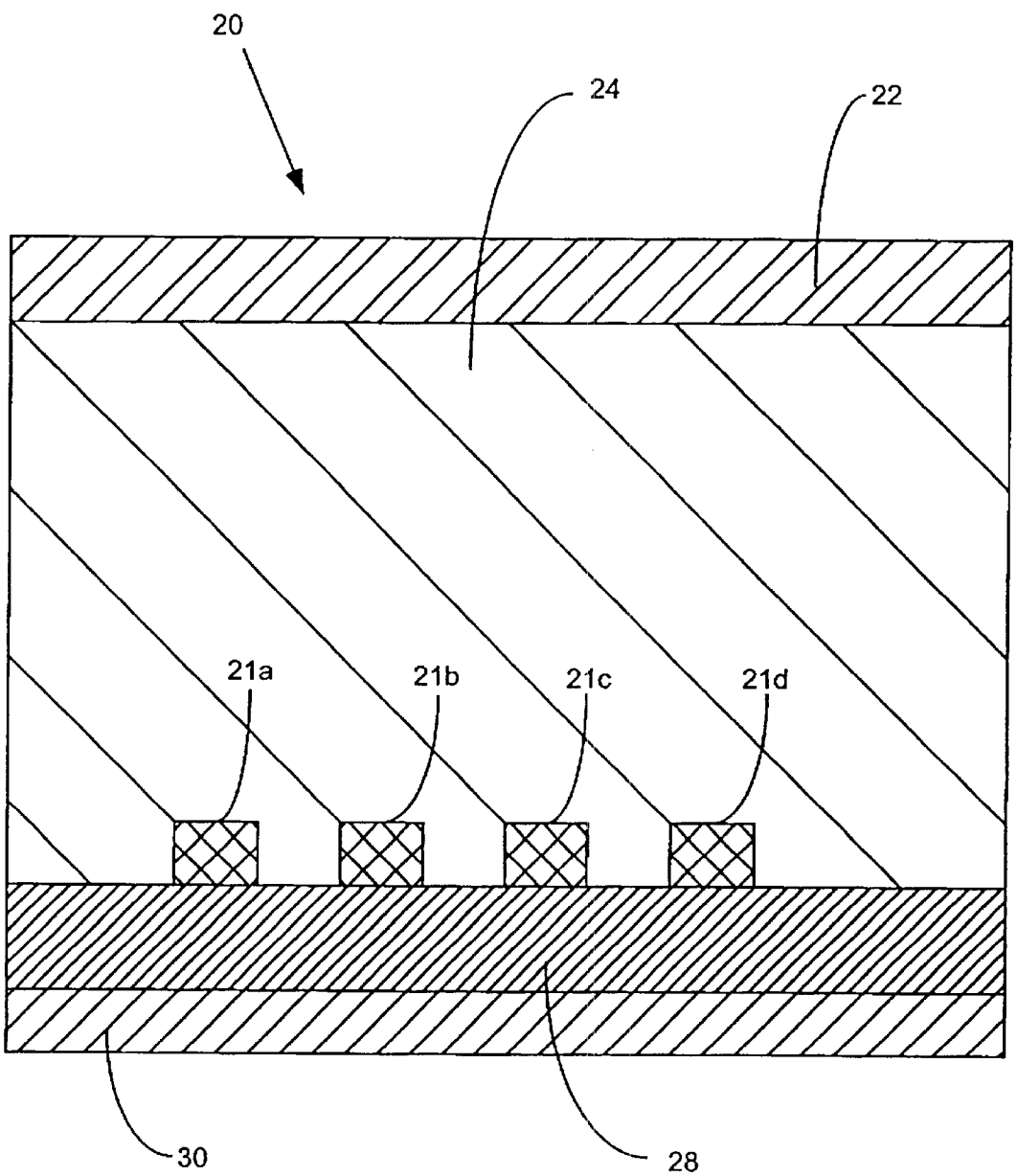
FIG. 2 illustrates a cross-sectional view of an improved flexible plethysmographic transducer of the present invention having four electrodes.

FIG. 2 illustrates a cross-sectional view of flexible plethysmograph transducer 20 of the present invention. Transducer 20 can be used to detect extravasation during injection of a fluid into a patient as previously described. Four electrodes 21a–d are preferably provided within transducer 20 for applying and measuring energy. In transducer 20, electrodes 21a–d can be disposed upon the surface of high dielectric layer 28 for efficient capacitive coupling to the patient in the vicinity or region of an injection site. High dielectric layer 28 provides high capacitive coupling between electrodes 21a–d and the patient. The opposing surface of high dielectric layer 28 can be coated with layer 30 of hydrogel to further improve electrical coupling of electrodes 21a–d to the patient.

A low dielectric layer 24 is preferably disposed over electrodes 21a–d and high dielectric layer 28. In this manner the various layers of transducer 20 can serve as a substrate for applying electrodes 21a–d to the patient. A high conductivity layer 22 is preferably disposed over low dielectric layer 24. High conductivity layer 22 functions as a ground plane for plethysmograph transducer 20. The ground plane provided by high conductivity layer 22 shields electrodes 21a–d from stray capacitance and provides a more reliable measurement of the impedance in the region of the injection site.

Figure 3A:
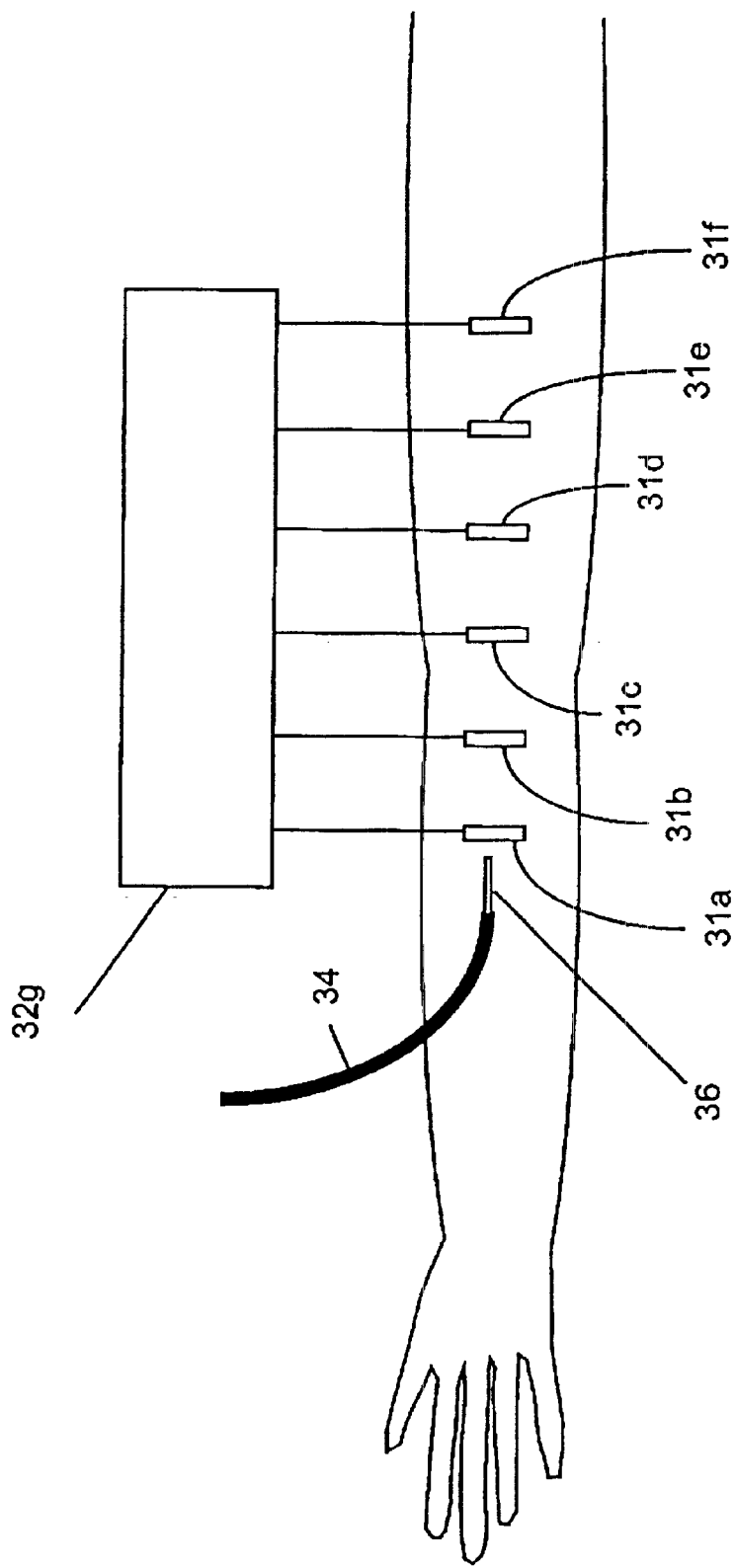
FIG. 3A illustrates an array of plethysmographic transducers or sensors that enable detection of extravasation beyond the immediate injection site.

Extravasation typically occurs in the immediate vicinity of the injection site (usually the antecubital vein of the arm). In some patients, however, extravasation sometimes occurs at a site remote from the catheter insertion point (that is, the injection site). This remote extravasation can result, for example, from weakened vessel walls or valve disease. To detect such remote extravasation, a plurality of plethysmograph sensors or transducers as illustrated in FIG. 3A can be applied to the patient at locations in the vicinity of and/or remote from the injection site. It is thus possible to detect extravasation that may occur at the remote locations as a result of injection of the fluid into the patient at the injection site.

With such an array, it is possible to improve the utility of the impedance plethysmograph by arranging several electrodes along the limb in, for example, a linear array 31a–f as shown in FIG. 3A. In this array, any two outer electrodes can be connected as the source and sink of RF current, while any two "inner" electrodes positioned between the outer pair can be used for voltage measurement. A set of switches and processing electronics 32g can determine which pairs of electrodes to use for the measurement to sense extravasations occurring downstream from the actual injection site. For example, at the beginning of an injection, the array might use electrode pair 31a.d to provide current and electrode pair 31b.c to sense voltage. An early extravasation occurring at the start of an injection close to the needle entry site can be sensed immediately below this electrode arrangement. However, later in an injection, when fluid pressure builds up in a vein, an extravasation is also likely to occur far from the injection site, perhaps near a valve compromised by vascular disease. To detect this event, the electronic control 32g can switch in/on the outer electrode pair 31a.f and any of the inner electrode pairs such as 31b.c, 31b.d, 31c.e for example. This control allows detection capability over an extensive region of tissue or more focused examination anywhere between the outer electrode pair.

Figure 3B:
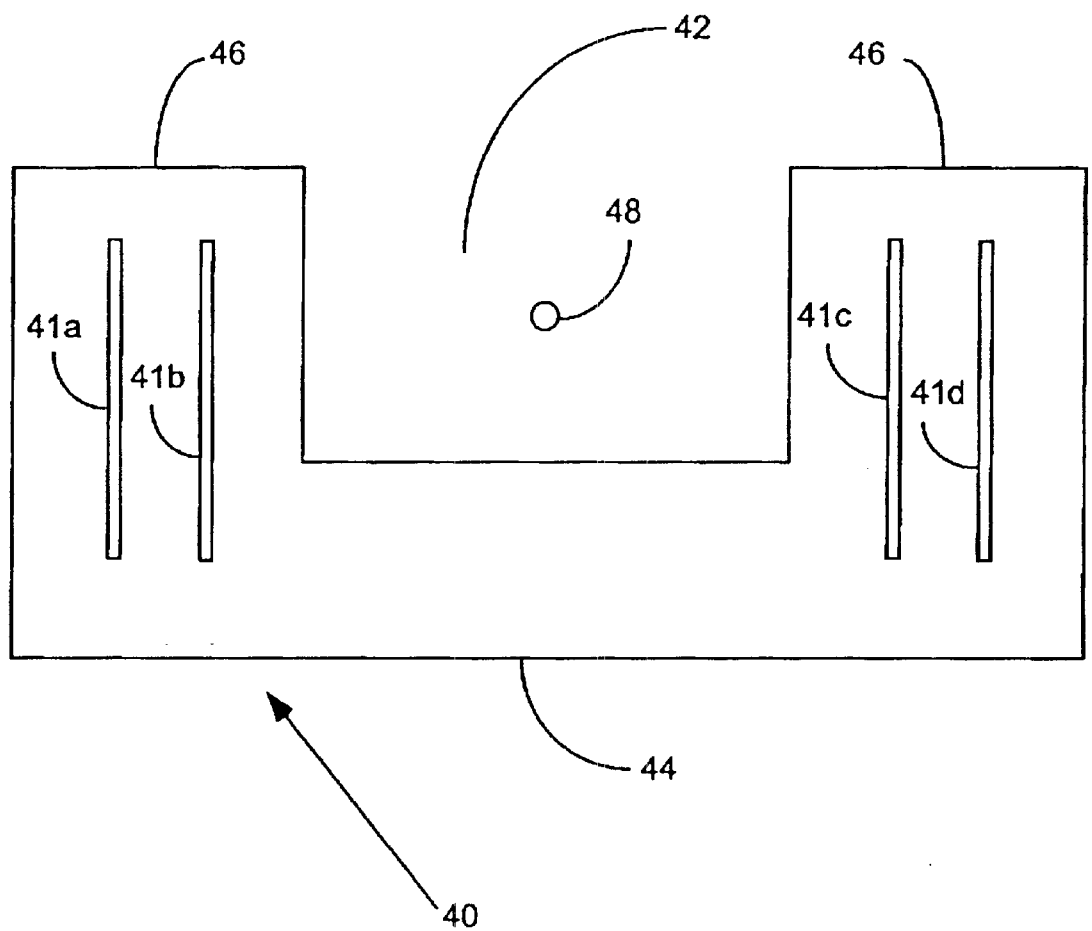
FIG. 3B illustrates another embodiment of a plethysmographic transducer of the present invention having an open region to allow palpation and visual observation of the region or vicinity of the injection site.

FIG. 3B illustrates another embodiment of a plethysmograph transducer 40 of the present invention. plethysmograph transducer 40 can be used to detect extravasation during injection of a fluid into a patient at injection or other site 48 as previously described. Four electrodes 41a–d are provided within plethysmograph transducer 40 for applying and measuring energy. Plethysmograph transducer 40 is also provided with cutaway or open region 42 that defines two electrode bearing portions 46. Electrode bearing portions 46 may be joined together by a bridge region 44 that is also defined by open region 42. Electrodes 41a and 41b are fixed to one electrode bearing portion 46 of plethysmograph transducer 40 and electrodes 41c and 41d are fixed to the other electrode bearing portion 46.

When plethysmograph transducer 40 is applied to a patient to detect extravasation, it is disposed to position electrodes 41a and 41b on one side of injection site 48 and to position electrodes 41c and 41d on a different side of injection site 48. When electrodes 41a–d are positioned in this manner, bridge 44 is disposed along a side of the vicinity of injection site 48. Thus, open region 42 is disposed over the region of the patient in the vicinity of injection site 48. Because the vicinity of injection site 48 is exposed and maintained in an uncovered state, it is available for palpation and visual observation while energy is applied to the vicinity of injection site 48 to assist in detecting extravasation.

In an alternate embodiment of plethysmograph transducer 40, bridge region 44 can be removed and electrode bearing regions 46 can operate as two separate electrode bearing regions 46 or patches. It is thus possible to position electrodes 41a and 41d of one electrode bearing portion 46 on one side of injection site 48 and electrodes 41c and 41d of the other, separate electrode bearing portion 46 on the other side, while leaving the vicinity of injection site 48 available for palpation and visual observation as previously described.

Figure 4:
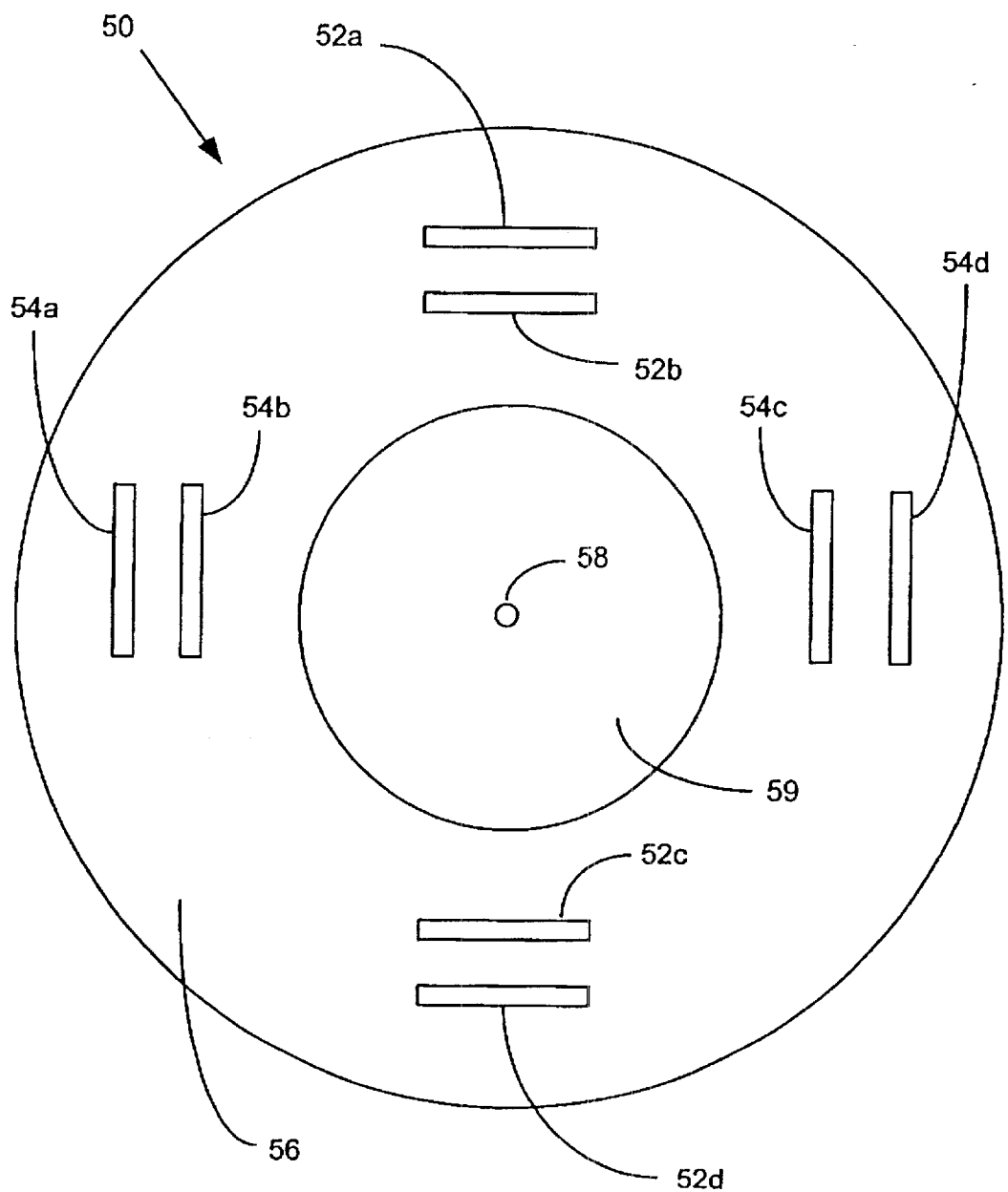
FIG. 4 illustrates another embodiment of a plethysmographic transducer of the present invention having electrodes that are orthogonally disposed upon a generally circular substrate.

FIG. 4 illustrates another embodiment of a plethysmograph transducer 50 of the present invention which can be used to detect extravasation during injection of a fluid into a patient as previously described. In this embodiment, electrodes 52a–d and electrodes 54a–d are generally orthogonally disposed upon plethysmograph transducer 50 for applying RF electrical energy. Plethysmograph transducer 50 preferably includes an annular substrate 56 upon which electrodes 52a–d and electrodes 54a–d are disposed. Annular substrate 56 defines an open region 59 in the vicinity of injection or other site 58. As discussed above, open region 59 permits palpation and visual observation of the vicinity of injection site 58 during the injection procedure. A ground plane can be provided for substrate 56 to shield measurements performed using plethysmograph transducer 50 from stray capacitance as previously described.

Electrodes 52a and 52d and generally orthogonal electrodes 54a and 54d are preferably positioned to apply energy to region 59 in the vicinity of injection site 58. Electrodes 52b and 52c and generally orthogonal electrodes 54b and 54c are preferably adapted to perform impedance measurements of region 59 when energy is applied in this manner. In one embodiment, electrodes 52a and 52d and electrodes 54a and 54d apply energy of differing frequencies to facilitate separate energy measurements. Measurements from orthogonal electrode pairs can also be made alternately and sequentially. Measurements from electrode pairs of different orientation such as in plethysmograph transducer 50 can provide useful additional information because the resistivity of skeletal muscle tissue varies as a function of current flow between the outer electrodes. For example, tissue resistivity measured in the long axis of the arm (230 ohm-cm in the general orientation of muscle fiber sheaths) is about half the resistivity measured at right angles to this axis (470 ohm-cm). Geddes, L. A. and Baker, L. E., "The Specific Resistance of Biological Material," *Medical and Biological Engineering*, Vol. 5, pp.271–293 (1967). The electrode pairs are preferably positioned to be generally orthogonal to maximize such differences. By comparison of such measurements over different directions or orientations, the sensitivity of the device can be improved and artifacts arising from movement of the patient can be reduced or eliminated. This sensitivity improvement can be expected if the measurements arising from patient movement are smaller than the difference resulting from electrical measurements of resistance alone.

Substrate 56 of plethysmograph transducer 50 can have virtually any geometry suitable for positioning electrodes 52a–d and electrodes 54a–d around injection site 58 to create an open region that permits manual palpation and visual observation during injection. For example, substrate 56 can be a rectangle or an oval. Additionally, electrodes 52a–d and electrodes 54a–d can have an arcuate configuration or any other suitable configuration in addition to a linear configuration.

Figure 5:
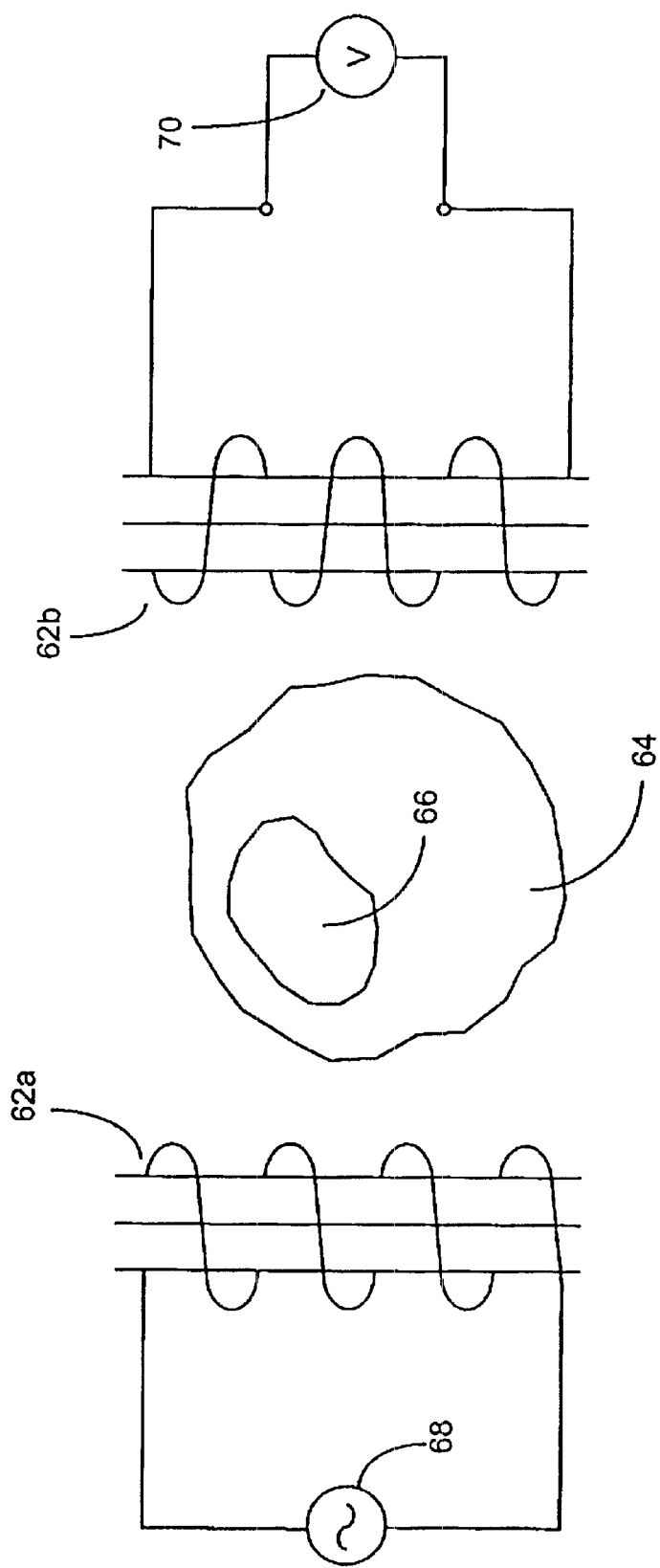
FIG. 5 illustrates a further embodiment of a plethysmographic transducer of the present invention wherein the mutual inductive coupling of a pair of electrically conducting coils is changed as a result of induced circulating eddy currents in tissue into which injection fluid is extravasated.
Figure 6:
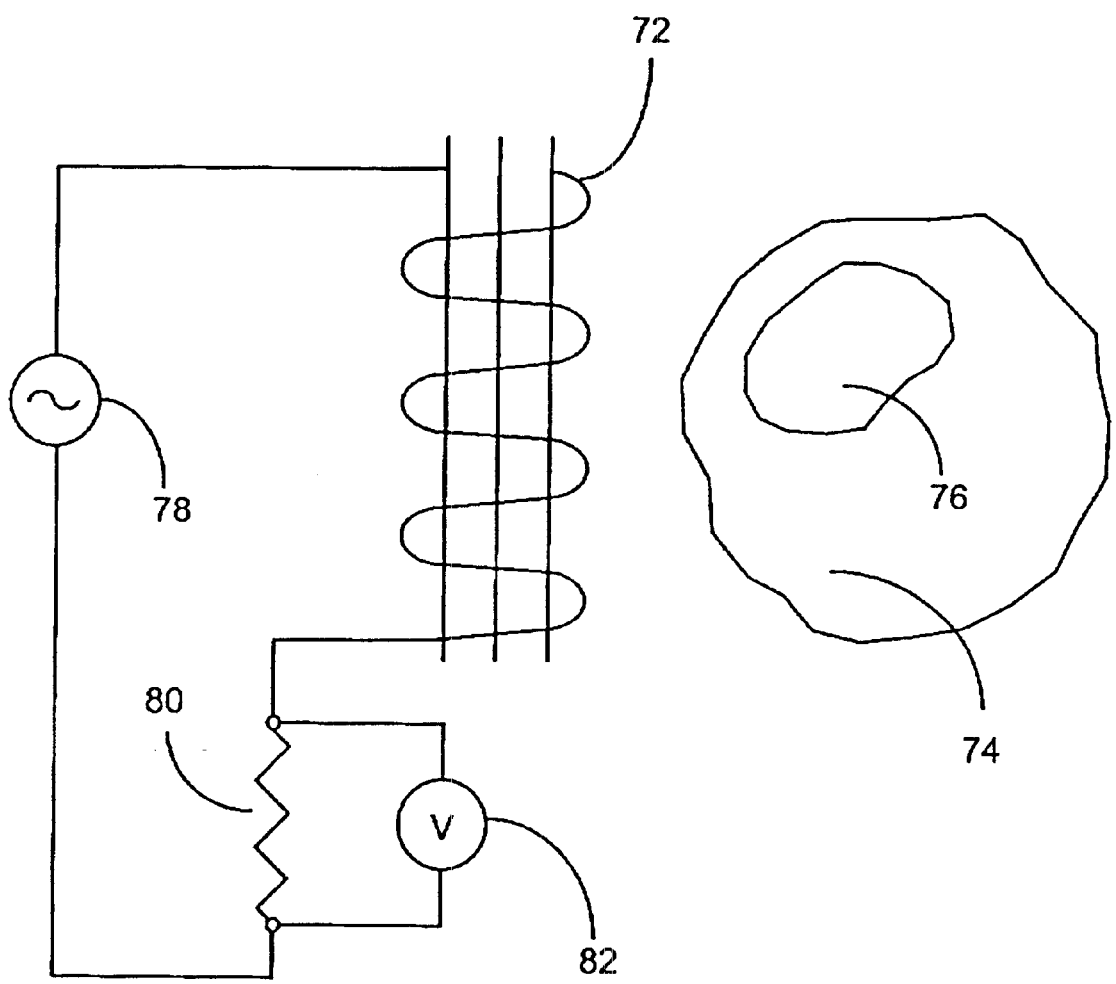
FIG. 6 illustrates a single electrically conductive coil whose inductance changes as a result of circulating eddy currents induced in tissue.

In the embodiments of FIGS. 5 and 6, the vicinity of the injection site is maintained in an unobstructed state for palpation and/or visual observation through use of detection devices that do not require contact with the patient. In that regard, it is not necessary to use electrodes adapted for measuring capacitive impedance within the plethysmographs of the present invention. Rather, it is possible to use inductance measuring electrodes because extravasation alters the inductive impedance of tissue of a region as well as the capacitance of the region.

As shown in FIG. 5, the inductance measuring electrodes for detecting an extravasation 66 can comprise two non-contacting coils 62a and 62b whose inductive coupling changes when circulating eddy currents are induced in tissue 64 of the patient by coils 62a and 62b. The coils 62a and 62b are preferably positioned in proximity to tissue 64 of the patient. In effect, conductive tissue 64 acts as a transformer coupling coils 62a and 62b. In the embodiment of FIG. 5, coil 62a is in electrical connection with a source of RE energy 68, while coil 62b is in electrical connection with a voltmeter 70 for measuring changes in inductive impedance.

In a preferred embodiment an inductance sensing coil can be made part of a tuned circuit. When extravasation occurs and the inductance of the sensing coil changes, the tuned circuit is detuned thereby permitting detection of the extravasation.

FIG. 6 illustrates an alternative embodiment of the present invention in which an extravasation 76 is detected through measurement of changes in the inductance of a single coil 72 resulting from circulating eddy currents in a region of conductive tissue 74. Coil 72 is preferably in electrical connection with circuitry comprising a source of RF energy 78, a sensing resistance 80 and a voltmeter 82. The coil 72 forms the primary side of a transformer which inductively couples RE energy into tissue. If a constant voltage source 78 is used, mutual coupling will result in a change in current in the primary that is measurable by voltmeter 82 across sampling resistor 80.

Although the present invention has been described in detail in connection with the above embodiments and/or examples, it is to be understood that such detail is solely for that purpose and that variations can be made by those skilled in the art without departing from the invention. The scope of the invention is indicated by the following claims rather than by the foregoing description. All changes and variations which come within the meaning and range of equivalency of the claims are to be embraced within their scope.

What is claimed is:

1. A system for the detection of extravasation in an injection procedure, the system comprising:
   a first sensor positioned to detect extravasation in the vicinity of an injection site; and
   at least a second sensor positioned to detect extravasation at a site other than in the vicinity the injection site.

2. The system of claim 1 wherein the first sensor comprises at least a first energy source to supply energy to tissue in the vicinity of an injection site, and at least a first receiver to measure a signal resulting from the energy supplied to the tissue by the first energy source, the first energy source and the first receiver being positioned in a manner so that the vicinity of the injection site is available for palpation and visible for visual inspection.

3. The system of claim 1 wherein the first sensor comprises at least a first energy source to supply energy to tissue and at least a first receiver to measure a first signal resulting from the energy supplied to the tissue by the first energy source.

4. The system of claim 3 wherein the at least a first energy source and the at least a first receiver are positioned in a manner so that the site is available for palpation.

5. The system of claim 3 wherein the first sensor further comprises a second energy source to supply energy to tissue and a second receiver for measuring a second signal resulting from the energy supplied to the tissue by the second energy source.

6. The system of claim 5 wherein the first energy source and first receiver pairing are orthoganally positioned with respect to the second energy source and second receiver pairing.

7. The system of claim 1 wherein the second sensor comprises at least a first energy source to supply energy to tissue, and at least a first receiver to measure a signal resulting from the energy supplied to the tissue by the first energy source.

8. The system of claim 1, further comprising a third sensor positioned to detect extravasation at a site other than in the vicinity of the injection site.

9. The system of claim 1 wherein the first sensor and the at least a second sensor are substantially disposed in a line along an area of a patient.

10. The system of claim 1 wherein the first sensor comprises a first coil and a second coil.

11. The system of claim 10 wherein the first coil is connected to a source of RF energy and the second coil is connected to a voltmeter for measuring changes in inductive impedance.

12. The system of claim 3 wherein the at least a first energy source and the at least a first receiver comprise a transceiver.

13. The apparatus of claim 3 wherein the at least a first energy source and the at least a first receiver are in ohmic contact with the skin of a patient.

14. The system of claim 1 wherein the first sensor or the at least a second sensor comprises at least a first energy source to supply energy to tissue and at least a first receiver to measure a first signal resulting from the energy supplied to the tissue by the first energy source.

15. The system of claim 14 wherein the at least a first energy source and the at least a first receiver are disposed on a base.

16. The system of claim 15 wherein the base comprises to opposing portions joined together by a bridge region.

17. The system of claim 16 wherein the bridge region and the two opposing portions define an open area.

18. A method for detecting extravasation in an injection procedure, the method comprising: positioning at least a first sensor adapted to detect extravasation at a position other than in the vicinity of an injection site along a path of potential extravasation.

19. The method of claim 18, further comprising the step of positioning a second sensor adapted to detect extravasation in the vicinity of the injection site.

20. The method of claim 19 wherein the second sensor comprises at least a first energy source to supply energy to tissue in the vicinity of an injection site, and at least a first receiver to measure a signal resulting from the energy supplied to the tissue by the first energy source, the first energy source and the first receiver being positioned in a manner so that the vicinity of the injection site is available for palpation and visible for visual inspection.

* * * * *